United States Patent
Tokunaga et al.

(10) Patent No.: US 6,872,835 B2
(45) Date of Patent: Mar. 29, 2005

(54) PROCESS FOR PREPARATION OF FUSED PYRROLES

(75) Inventors: Makoto Tokunaga, Wako (JP); Yasuo Wakatsuki, Wako (JP)

(73) Assignees: Japan Science & Technology Corporation, Saitama-Ken (JP); Riken, Saitama (JP)

( * ) Notice: Subject to any disclaimer, the term of this patent is extended or adjusted under 35 U.S.C. 154(b) by 193 days.

(21) Appl. No.: 10/088,276

(22) PCT Filed: Jul. 2, 2001

(86) PCT No.: PCT/JP01/05691

§ 371 (c)(1),
(2), (4) Date: Oct. 22, 2002

(87) PCT Pub. No.: WO02/06226

PCT Pub. Date: Jan. 24, 2002

(65) Prior Publication Data

US 2004/0049054 A1 Mar. 11, 2004

(30) Foreign Application Priority Data

Jul. 17, 2000 (JP) .................................. 2000-216457

(51) Int. Cl.$^7$ ........................................ C07D 209/04
(52) U.S. Cl. ........................................ 548/508
(58) Field of Search ........................................ 548/508

(56) References Cited

U.S. PATENT DOCUMENTS

| | | | |
|---|---|---|---|
| 2,703,333 A | 3/1955 | Rowlands | ............ 260/566 |
| 4,062,865 A | * 12/1977 | Moggi | ............ 548/508 |

FOREIGN PATENT DOCUMENTS

| | | |
|---|---|---|
| JP | 62-93273 | 4/1987 |
| JP | 5-286932 | 11/1993 |
| JP | 7-238069 | 9/1995 |
| JP | 2000-136182 | 5/2000 |

OTHER PUBLICATIONS

M. Tokunaga, et al., "A practical one–pot synthesis of 2, 3–disubstituted indoles from unactivated anilines", *Tetrahedron Letters* 42 (2001) 3865–3868.
M. Tokunaga, et al., "Ruthenium–Catalyzed Intermolecular Hydroamination of Terminal Alkynes with Anilines: A Practical Synthesis of Aromatic Ketimines", *Angew. Chem. Int. Ed 111*, (1999) 3408–3411, 1433–7851/99/3821–3224.
M. Fagnola et al., *Tetrahedron Letters*, 13:2307–2310 (1997).
J. Mahanty et al., *Tetrahedron*, 39:13397–13418 (1997).

\* cited by examiner

*Primary Examiner*—Johann Richter
*Assistant Examiner*—Ebenezer Sackey
(74) *Attorney, Agent, or Firm*—Peter F. Corless; John B. Alexander; Edwards & Angell, LLP

(57) ABSTRACT

The invention provides processes for the preparation of fused pyrroles, preferably indoles, which permit the use of inexpensive aromatic amines themselves as the raw material and attain high atomic efficiency and high regioselectivity. Specifically, a process for the preparation of fused pyrroles, e.g., indoles bearing methyl at the 3-position of pyrrole ring and $R^1$ (or $R^2$) of the general formula (4) at the 2-position thereof, or 3,3-disubstituted indoles bearing $R^1$ and $R^2$ at the 3-position of pyrrole ring and methyl at the 2-position thereof, characterized by reacting an alkynol of the general formula (4) with an aromatic primary amine in the presence of a ruthenium complex, more preferably with an acid or an ammonium salt thereof being made to coexist.

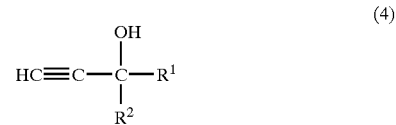

(4)

[In the general formula (4), $R^1$ and $R^2$ are each independently hydrogen, optionally substituted alkyl, or optionally substituted aryl, or alternatively $R^1$ and $R^2$ may be united to form an alkylene chain.]

11 Claims, No Drawings

PROCESS FOR PREPARATION OF FUSED PYRROLES

TECHNICAL FIELD

This invention relates to a novel process for producing condensed pyrroles useful as starting materials, intermediates etc. for dyes, perfumes etc. or as starting materials for synthesizing physiologically active substances.

BACKGROUND ART

There are many physiologically active substances containing a condensed pyrrole ring, and in particular new methods of producing substances containing an indole ring have been actively studied from the 19th century to the present. Besides the Fischer method known for 100 years or more, methods such as Bischler method, Madelung method, Reissert method and a method of using a palladium catalyst have been developed, but have not surpass the Fischer method in general and economical aspects.

The Fischer method is a method of synthesizing a hydrazone from an aryl hydrazine and a ketone and then treating it with an acid to form indole. Because various kinds of ketones are easily available, this method is generally usable, but there are problems such as necessity for synthesis of hydrazine from an aniline derivative and occurrence of various regioisomers at the time of forming an indole ring, etc. Various attempts have been made on regioselective synthesis, but have never provided complete solution (J. Org. Chem., 56, 3001(1991); J. Org. Chem., 58, 7638 (1993), etc.).

The reaction scheme of synthesizing indole by the Fischer method is shown below:

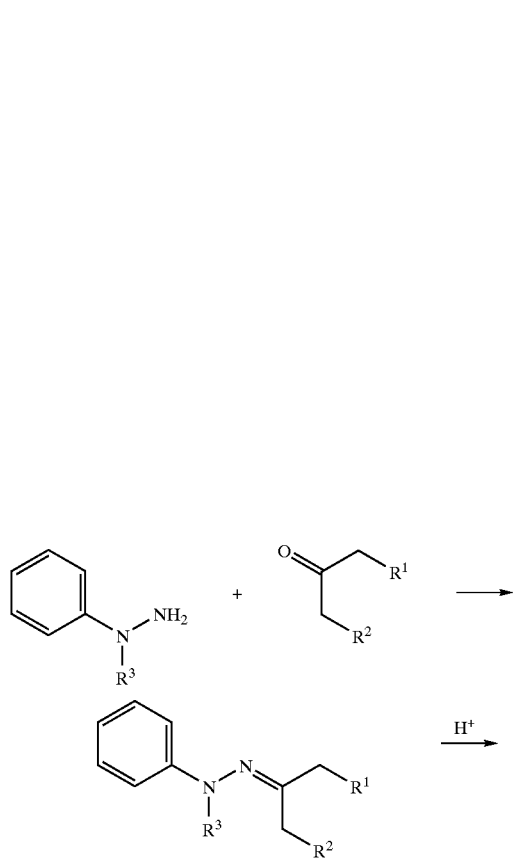

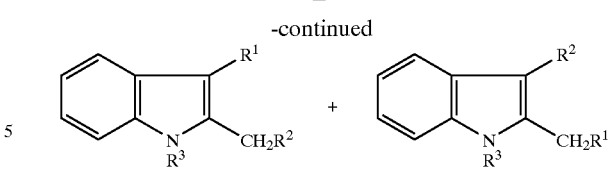

On the other hand, as organometallic chemistry has advanced for about 30 years, methods of using a palladium catalyst have been extensively developed. Such methods utilize the cross-coupling reaction unique to the palladium catalyst. These methods involve reacting o-iodoaniline with an alkyne etc. to synthesize o-alkynyl aniline and then adding an amine to the alkyne in the molecule to form an indole ring, and there are a vast number of reports thereon. The disadvantages of such methods are that o-iodoaniline is considerably more expensive than aniline; although the atomic weight of iodine is 127 which is higher than that (92) of the aniline nucleus, the iodine does not remain in the indole skeleton of the product and is discarded as a byproduct, that is, the atom efficiency is low; nitrogen in the aniline should previously been converted into e.g. amide (Chem. Pharm. Bull., 1305 (1988); Tetrahedron Lett., 3915 (1992), etc.).

The reaction scheme of synthesizing indole by the method of using a palladium catalyst is shown below:

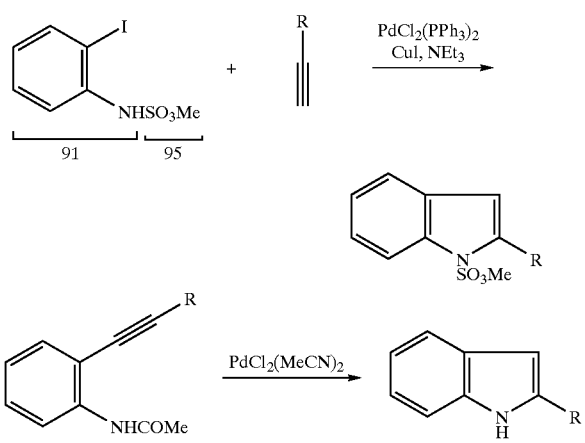

Further, as a method of using a ruthenium catalyst, a method of synthesizing indole from aniline and 1,2-diol is known. This method is superior in features such as atom efficiency and usability of aniline itself as a starting material, but there are problems such as formation of a mixture of isomers from asymmetric diol due to generally low regioselectivity, necessity for relatively high temperature (180° C.), necessity for an argon atmosphere, necessity for a solvent, etc. (J. Org. Chem., 52, 1673 (1987), etc.).

The reaction scheme of synthesizing indole by the method of using a ruthenium catalyst is shown below:

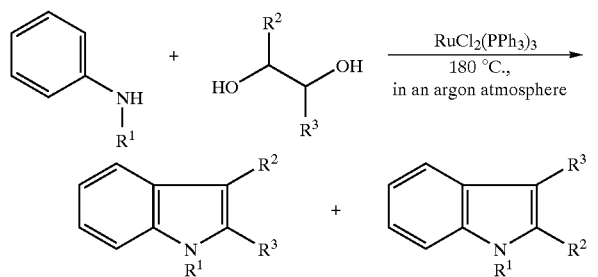
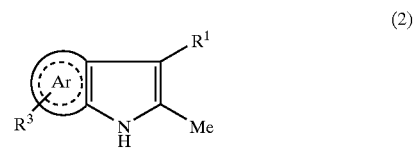

DISCLOSURE OF INVENTION

This invention was made in view of the present circumstances described above, and the object of this invention is to provide a process for producing condensed pyrroles having high regioselectivity, preferably indoles, which achieves high atom efficiency and can utilize inexpensive aromatic amines itself as the starting material.

BEST MODE FOR CARRYING OUT THE INVENTION

This invention relates to a process for producing condensed pyrroles, which comprises allowing an alkyne alcohol represented by formula (4):

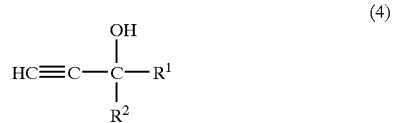

wherein $R^1$ and $R^2$ independently represent a hydrogen atom, an alkyl group which may have a substituent group or an aryl group which may have a substituent group, and $R^1$ and $R^2$ are combined to form an alkylene chain, to react with an aromatic primary amine in the presence of a ruthenium complex.

For example, the compounds obtained by the process of this invention include:

the compound represented by the general formula (1) (referred to hereinafter as Compound (1)):

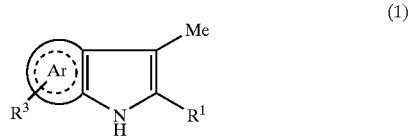

wherein double-circled Ar represents an aromatic ring, $R^1$ (or $R^2$) represents a hydrogen atom, an alkyl group which may have a substituent group or an aryl group which may have a substituent group, and $R^3$ represents an alkyl group which may have a substituent group, an aryl group, a hydroxy group, an alkoxy group, an amide group, a ketone group, an ester group or a halogeno group;

the compound represented by the general formula (2) (referred to hereinafter as Compound (2)):

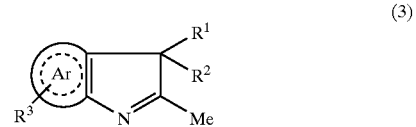

wherein double-circled Ar represents an aromatic ring, $R^1$ (or $R^2$) represents a hydrogen atom, an alkyl group which may have a substituent group or an aryl group which may have a substituent group, and $R^3$ represents an alkyl group which may have a substituent group, an aryl group, a hydroxy group, an alkoxy group, an amide group, a ketone group, an ester group or a halogeno group; and the compound represented by the general formula (3) (referred to hereinafter as Compound (3)):

$$\text{(3)}$$

wherein double-circled Ar represents an aromatic ring, $R^3$ represents an alkyl group which may have a substituent group, an aryl group, a hydroxy group, an alkoxy group, an amide group, a ketone group, an ester group or a halogeno group, and $R^1$ and $R^2$ have the same meanings as defined above.

In the general formula (4), when $R^1$ and/or $R^2$ is a hydrogen atom, the product is Compound (1) and/or (2), and when both $R^1$ and $R^2$ are other than hydrogen atom, the product is Compound (3).

In the alkyne alcohols represented by the general formula (4) used in the invention, the alkyl group in the optionally substituted alkyl group represented by $R^1$ and $R^2$ includes e.g. a $C_{1-20}$ linear or branched alkyl group such as methyl group, ethyl group, propyl group, butyl group, pentyl group, hexyl group, heptyl group, octyl group, nonyl group, decyl group, dodecyl group, pentadecyl group, hexadecyl group, octadecyl group, nonadecyl group and eicosyl group. The aryl group in the optionally substituted aryl group includes e.g. a phenyl group, tolyl group, xylyl group, naphthyl group, methyl naphthyl group, biphenyl group etc. The substituent groups on these alkyl and aryl groups include e.g. an alkoxy group such as methoxy group and ethoxy group, an alkenyl group such as vinyl group and allyl group, a halogeno group such as chloro group, bromo group and fluoro group, and an amide group, an ester group etc.

When $R^1$ and $R^2$ are combined to form an alkylene chain, these groups together with their adjacent C atom form e.g. a cyclopropane ring, cyclopentane ring, cyclohexane ring etc.

The aromatic primary amines used in the invention include e.g. aniline and nucleus-substituted derivatives thereof, 1- or 2-naphthyl amine and nucleus-substituted derivatives thereof, 1- or 2-aminoanthracene and nucleus-substituted derivatives thereof, and 2-aminobiphenyl and nucleus-substituted derivatives thereof.

In the formulae (1), (2) and (3), the double-circled Ar represents an aromatic ring, and the aromatic ring referred to herein may be a monocyclic, condensed polycyclic, non-condensed polycyclic carbon ring or heterocyclic ring, and includes e.g. a benzene ring, naphthalene ring, anthracene ring, phenanthrene ring, biphenyl, terphenyl, pyridine ring, pyrimidine ring etc. The heterocyclic ring is preferably a ring having 1 to 3 heteroatoms such as O, S and N.

The alkyl group in the optionally substituted alkyl group represented by $R^3$, that is, a substituent group on the aromatic ring mentioned above, includes e.g. a $C_{1-6}$ linear or branched lower alkyl group such as methyl group, ethyl group, propyl group, butyl group, pentyl group and hexyl group, and the substituent group thereon includes a hydroxyl group, an alkoxy group such as methoxy group, ethoxy group, n-propoxy group and isopropoxy group, and a halogen atom such as chlorine, bromine and fluorine.

The aryl group represented by $R^3$ includes e.g. a phenyl group, tolyl group, xylyl group, naphthyl group, methyl naphthyl group, biphenyl group etc., and the alkoxy group represented by $R^3$ includes e.g. a methoxy group, ethoxy group, n-propoxy group, isopropoxy group, n-butoxy group, t-butoxy group etc., and the halogeno group represented by $R^3$ includes e.g. a chloro group, bromo group, fluoro group etc.

In addition to those described above, other substituent groups represented by $R^3$ on the aromatic ring include a hydroxy group, amide group, ketone group, ester group etc.

Among the aromatic primary amines having these substituent groups, those aromatic primary amines having electron-donating substituent groups such as hydroxy group and alkoxy group are particularly highly reactive, thus giving high yield.

The ruthenium complex used in the process of this invention may be any complex capable of demonstrating a catalytic action in reaction of the alkyne alcohol with the aromatic primary amine, and for example, use can be made of ruthenium complexes used in conventional processes for producing an imine and enamine by adding e.g. an amine to a terminal alkyne.

The ruthenium complexes usable in this invention include e.g. $Ru_3(CO)_{12}$, $Ru(CO)_3(C_8H_{12})$, $Ru(CO)_3(C_8H_8)$, $[RuCl_2(CO_3)]_2$, $[Ru(C_5H_5)(CO)_2]_2$, $(C_2H_5)_4N.[HRu_3(CO)_{12}]$, $HRu_4(CO)_{12}$, $[(C_2H_5)_4N]_2.[Ru_6C(CO)_{16}]$, $[(Ph_3P)_2N]_2.[Ru_6(CO)_{18}]$, $[(Ph_3P)_2N]_2.[Ru_{10}C(CO)_{24}]$, $[RuCl_2(C_6H_6)]_2$, $RuCl_3.3H_2O$, $[RuCl_2(PPh_3)_3]$, $[RuCl_2(C_6H_6)(PPh_3)]$, $[RuCl_2(C_6H_6)(PBu_3)]$, $RuCl_2(C_6H_6)(P(C_6F_5)_3)$, etc. In these formulae, Ph represents a phenyl group, and Bu represents a butyl group.

The ruthenium complex is particularly preferably $Ru_3(CO)_{12}$. The amount of the ruthenium complex added to the reaction system is usually 0.1 to 10 mol-%.

The process of this invention is conducted preferably in the coexistence of an acid or an ammonium salt thereof (referred to hereinafter as "additive").

Depending on the type of the aromatic primary amine used as the starting material, the amount of the additive is not necessarily the same, but generally speaking, when e.g. $Ru_3(CO)_{12}$ is used as the ruthenium complex, the additive is used in an amount of about 3 equivalents relative to $Ru_3(CO)_{12}$ (that is, in an amount of about 1 equivalent relative to the ruthenium atom), whereby the compounds represented by the following general formula (5):

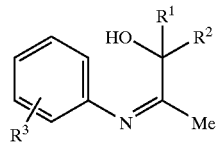

(5)

(wherein the double-circled Ar, $R^1$, $R^2$ and $R^3$ have the same meanings as defined above) are obtained, while the additive is used in excess, for example in an amount of 10 equivalents or more relative to $Ru_3(CO)_{12}$ (that is, in an amount of 3 equivalents or more relative to the ruthenium atom), the desired condensed pyrroles can be obtained. That is, the additive promotes both the first and second reactions. A small amount of the additive suffices for the first reaction, but a relatively large amount thereof is necessary for the second reaction. When the additive is used in an amount of 3 to 30 equivalents relative to $Ru_3(CO)_{12}$ (that is, in an amount of 1 to 10 equivalents relative to the ruthenium atom), the product is considered to occur as a mixture of the condensed pyrrole and an intermediate thereof, but formation of the product depends on the type of the aromatic primary amine used. This is because there is the case where even if the amount of the additive is low, the pyrrole ring is also formed depending on the type of the aromatic primary amine used (for example, m-hydroxy aniline can be easily cyclized to form indole in high yield even if the amount of the additive is 3 equivalents relative to $Ru_3(CO)_{12}$ (1 equivalent relative to the ruthenium atom).

Depending on the reaction conditions, the process of this invention can make use of a 2-stage reaction process wherein the compound represented by the general formula (5) above is first obtained from the alkyne alcohol and the aromatic primary amine, and then converted into the desired condensed pyrrole, or a process wherein the alkyne alcohol and the aromatic primary amine are converted directly into the condensed pyrrole. In the case of the 2-stage synthesis, the compound represented by the general formula (5) may be isolated once, or without isolation, the reaction mixture may be used as such in the second reaction. When the intermediate is isolated, further addition of the ruthenium complex and the additive is naturally necessary for conducting the next reaction, but when the reaction mixture is subjected as such without isolation to the second reaction, it is enough to add a deficient amount of the additive.

As the additive, almost all acids and ammonium salts thereof are effective. Generally, stronger acidic additives tend to be highly effective, however among hydrohalogenic acids, HF and its ammonium salt are the most effective. Specifically, the acids include e.g. $HPF_6$, $HBF_4$, $BF_3$, $CF_3SO_3H$, $CH_3SO_3H$, $C_6H_6SO_3H$, $CH_3C_6H_6SO_3H$, $H_2SO_4$, HI, HBr, HCl, HF, $CF_3COOH$, $ClCH_2COOH$, $CH_3COOH$, $C_6H_5COOH$ etc., and effective ammonium salts are those except for quaternary ones ($N(CH_3)_4^+$ etc.). That is, unsubstituted ammonium salts ($NH_4^+$ salts), primary ammonium salts (for example $C_6H_5NH_3^+$ salt etc.), secondary ammonium salts (for example $NH_2(C_2H_5)_2^+$ salt etc.), tertiary ammonium salts (for example $NH(C_2H_5)_3^+$ salt etc.) have the same effect.

Usually, the additive preferably used is a salt consisting of the aromatic primary amine used in the reaction and one of the above acids.

The reaction is conducted usually under heating at 80 to 200° C. Replacement of the atmosphere in the reaction system by e.g. nitrogen or argon is not particularly necessary.

This reaction does not particularly necessitate the presence of a solvent, but can also be conducted using a general organic solvent. Preferable examples of the solvent includes those having a boiling point of 80° C. or more, such as ethylene glycol, grime, digrime, toluene, benzene, xylene, 2-propanol, 1,4-dioxane, dimethylformamide and dimethyl sulfoxide.

The method of isolating the condensed pyrrole as the final product can be conducted using an extraction procedure. That is, an excess of the aromatic primary amine etc. can be removed by adding an extraction solvent such as diethyl ether, dichloromethane and toluene to the reaction solution and then washing the product several times with e.g. 1 M hydrochloric acid. In this procedure, the product can usually attain 90 to 99% purity. The product can be further purified by re-crystallization, distillation etc.

In the process of this invention, when a primary or secondary alcohol is used as the starting alkyne alcohol, that is, when the alkylene alcohol of the general formula (4) wherein $R^1$ and/or $R^2$ is a hydrogen atom is used, Compound (1) is obtained as the major final product.

Compound (1) has a methyl group as a substituent group at the 3-position of the pyrrole ring and $R^1$ (or $R^2$) as a substituent group at the 2-position. Although Compound (2) wherein the substituent groups at the 2- and 3-positions have been replaced with each other is also simultaneously formed in a smaller amount, Compound (1) can be obtained as the major product. Compound (1): Compound (2) is usually at least 9:1.

In the process of this invention, when a tertiary alcohol is used as the starting alkyne alcohol, that is, when the alkylene alcohol of the general formula (4) wherein both $R^1$ and $R^2$ are other than hydrogen atom is used, Compound (3) i.e. a 3,3-di-substituted compound having $R^1$ and $R^2$ as substituent groups at the 3-position of the pyrrole ring and a methyl group at the 2-position is obtained as the final product.

The reaction scheme of the process of this invention is shown below by reference to an example wherein an aniline derivative is used as the aromatic primary amine.
(A) When the alkyne alcohol used is the alkyne alcohol of the general formula (4) wherein $R^2$ is a hydrogen atom

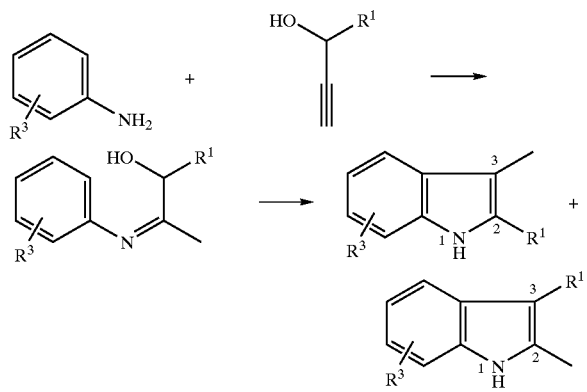

(B) When the alkyne alcohol used is the alkyne alcohol of the general formula (4) wherein both $R^1$ and $R^2$ are other than hydrogen atom

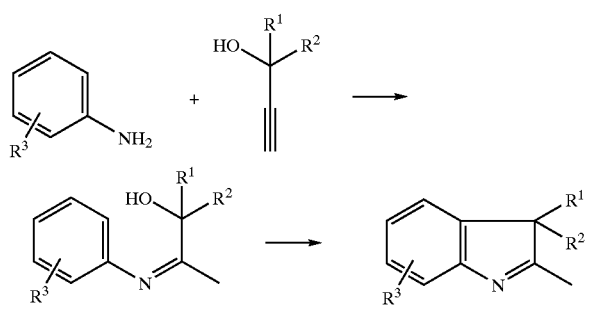

EXAMPLES

Hereinafter, this invention is described in more detail by reference to the Examples, which however are not intended to limit this invention.

Confirmation of the products in the Examples below was conducted by $^1$H NMR and GC-MS.

Example 1

Synthesis of 2,3-dimethyl indole by using a $Ru_3(CO)_{12}$ catalyst

3-Butine-2-ol (0.701 g, 10 mmol), aniline (0.931 g, 10 mmol), $Ru_3(CO)_{12}$ (32.0 mg, 0.05 mmol) and aniline hydrochloride (0.259 g, 2.0 mmol) were placed in a 10 ml round-bottomed flask, and the mixture was stirred at 120° C. for 12 hours. After cooling, dichloromethane (3 mL) was added, and the organic layer was washed twice with 1 M hydrochloric acid (2 mL) and once with water (2 mL). The organic layer was dried over sodium sulfate, and the solvent was distilled away, whereby 2,3-dimethyl indole (1.31 g; 9.0 mmol; yield, 90%; purity, about 99%) was obtained.

Example 2

Synthesis of 3-methyl-2-pentyl indole by Using a $Ru_3(CO)_{12}$ Catalyst

1-Octyne-3-ol (1.136 g, 9 mmol), aniline (0.559 g, 6 mmol), $Ru_3(CO)_{12}$ (16.0 mg, 0.025 mmol) and aniline hydrochloride (0.130 g, 1.0 mmol) were placed in a 10 ml round-bottomed flask, and the mixture was stirred at 140° C. for 9 hours. After cooling, diethyl ether (3 mL) was added, and the organic layer was washed twice with 1 M hydrochloric acid (2 mL) and once with water (2 mL). The organic layer was dried over sodium sulfate, and the solvent was distilled away, whereby an 11:1 mixture of 3-methyl-2-pentyl indole and 2-methyl-3-pentyl indole (1.262 g; 6.3 mmol; yield, 95%; purity, about 95% or more) was obtained.

Example 3

Synthesis of 2-ethyl-3-methyl Indole by Using a $Ru_3(CO)_{12}$ Catalyst

1-Pentine-3-ol (0.757 g, 9 mmol), aniline (0.559 g, 6 mmol), $Ru_3(CO)_{12}$ (16.0 mg, 0.025 mmol) and aniline hydrochloride (0.130 g, 1.0 mmol) were placed in a 10 ml round-bottomed flask, and the mixture was stirred at 140° C. for 7.5 hours. After cooling, dichloromethane (3 mL) was added, and the organic layer was washed twice with 1 M hydrochloric acid (2 mL) and once with water (2 mL). The organic layer was dried over sodium sulfate, and the solvent was distilled away, whereby a 9.3:1 mixture of 2-ethyl-3-methyl indole and 3-ethyl-2-methyl indole (1.06 g; 6.67 mmol; yield, 95%) was obtained.

Example 4

Synthesis of 2-methyl-3H-indole-3-spiro-1'-cyclohexane by Using a $Ru_3(CO)_{12}$ Catalyst 1-Ethynyl-1-cyclohexanol (1.242 g, 10 mmol), aniline (0.931 g, 10 mmol), $Ru_3(CO)_{12}$ (32.0 mg, 0.05 mmol) and aniline hydrochloride (0.259 g, 2.0 mmol) were placed in a 10 ml round-bottomed flask, and the mixture was stirred at 120° C. for 12 hours. After cooling, dichloromethane (3 mL) was added, and the organic layer was washed twice with 1 M hydrochloric acid (2 mL) and once with water (2 mL). The organic layer was dried over sodium sulfate, and the solvent was distilled away, whereby 2-methyl-3H-indole-3-spiro-1'-cyclohexane (24 mg; 0.12 mmol; yield, 1.2%; purity, 95% or more) was obtained.

Examples 5 to 12

Synthesis of Various Indoles by Using a $Ru_3(CO)_{12}$ Catalyst

In the following reaction scheme, $R^1$ and $R^3$ were replaced respectively by various groups shown in Table 1 below, and the reaction was conducted under the reaction conditions shown in Table 1, followed by post-treatment in accordance with the methods described in Examples 1 to 3, to give the results shown in Table 1.

that 3-methyl-2-alkyl indole which cannot be obtained in the Fischer method can be selectively obtained.]; and (iii) The atom efficiency in the reaction is very high, and as the reaction proceeds, one molecular of water is merely formed, and thus the influence of the reaction on the environment is also low.

TABLE 1

| Examples | $R^1$ | $R^3$ | 1/Additive/2 (mmol) | Time (h) | Yield (%) | 3a/3b |
|---|---|---|---|---|---|---|
| 5[c] | H | Ph | 6.0/1.0[a]/9.0 | 7[c] | >95 | 1/16 |
| 6[e] | m-OH | $CH_3$ | 6.0/1.0[a]/9.0 | 8[a] | 50 | — |
| 7[c] | p-$CH_3O$ | $CH_3$ | 6.0/1.0[a]/9.0 | 8[c] | 89 | — |
| 8[e] | 3,4-di-($CH_3O$) | n-$C_3H_7$ | 5.0/1.0[a]/7.0 | 24[e] | 75 | — |
| 9[c] | p-$CH_3$ | $C_2H_5$ | 6.0/1.0[a]/9.0 | 9[c] | 97 | 1/8.4 |
| 10[e] | o-$CH_3$ | $CH_3$ | 7.0/0.75[b]/9.0 | 17[e] | 91 | — |
| 11[e,f] | p-Cl | $CH_3$ | 5.0/0.75[b]/7.0 | 9[e] | 80 | — |
| 12[e,g] | o-$CO_2CH_3$ | $CH_3$ | 7.0/0.7[b]/9.0 | 23[e] | 40 | — |

[a]The corresponding monohydrochloride was used.
[b]$NH_4PF_6$ was used.
[c]No solvent was used.
[e]Ethylene glycol was used as solvent.
[f]0.5 mol-% catalyst was used.
[g]1.0 mol-% catalyst was used.

Example 13

Synthesis of 2,3-dimethylbenzo[g]indole by Using a $Ru_3(CO)_{12}$ Catalyst

3-Butine-2-ol (0.631 g, 9 mmol), 1-napthylamine (0.859 g, 6 mmol), $Ru_3(CO)_{12}$ (16.0 mg, 0.025 mmol), ammonium hexafluorophosphate (0.041 g, 0.25 mmol) and 1 ml ethylene glycol were placed in a 10 ml round-bottomed flask, and the mixture was stirred at 140° C. for 20 hours. After cooling, diethyl ether (3 mL) was added, and the organic layer was washed twice with 1 M hydrochloric acid (2 mL) and once with water (2 mL). The organic layer was dried over sodium sulfate, and the solvent was distilled away, whereby 2,3-dimethylbenzo[g]indole (1.113 g; 5.7 mmol; yield, 95%; purity, 95% or more) was obtained.

INDUSTRIAL APPLICABILITY

The advantages of the process of this invention are as follows:

(i) An inexpensive aromatic amine itself, for example aniline itself can be utilized as the starting material;

(ii) The regioselectivity in the reaction is so high that the product having a methyl group at the 3-position of the pyrrole ring and $R^1$ (or $R^2$) in the general formula (4) as a substituent group at the 2-position can be selectively obtained. [It is known that in the Fischer method, regio-control is generally difficult, but when 2-alkanone (methyl alkyl ketone) is used, 2-methyl-3-alkyl indole is predominantly obtained while 3-methyl-2-alkyl indole cannot be obtained. The outstanding advantage of this reaction is

What is claimed is:

1. A process for producing condensed pyrroles, which comprises contacting an alkyne alcohol represented by formula (4):

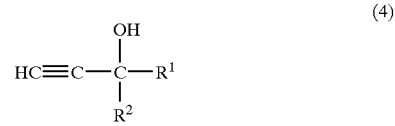

(4)

wherein $R^1$ and $R^2$ independently represent a hydrogen atom, an alkyl group which may have a substituent group or an aryl group which may have a substituent group, and $R^1$ and $R^2$ may be combined to form an alkylene chain, to react with an aromatic primary amine in the presence of a ruthenium complex.

2. The process according to claim 1, wherein the condensed pyrroles are compounds represented by formula (1):

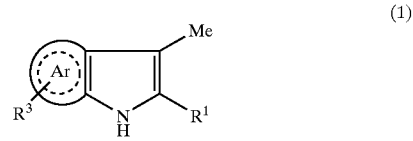

(1)

wherein double-circled Ar represents an aromatic ring, $R^1$ represents a hydrogen atom, an alkyl group which may have a substituent group or an aryl group which may have a substituent group, and $R^3$ represents an alkyl group which may have a substituent group, an aryl group, a hydroxy group, an alkoxy group, an amide group, a ketone group, an ester group or a halogeno group.

3. The process according to claim 1, wherein the condensed pyrroles are compounds represented by formula (2):

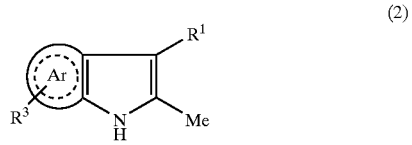

(2)

wherein double-circled Ar represents an aromatic ring, $R^1$ represents a hydrogen atom, an alkyl group which may have a substituent group or an aryl group which may have a substituent group, and $R^3$ represents an alkyl group which may have a substituent group, an aryl group, a hydroxy group, an alkoxy group, an amide group, a ketone group, an ester group or a halogeno group.

4. The process according to claim 1, wherein the condensed pyrroles are compounds represented by formula (3):

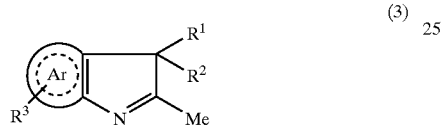

(3)

wherein double-circled Ar represents an aromatic ring, $R^3$ represents an alkyl group which may have a substituent group, an aryl group, a hydroxy group, an alkoxy group, an amide group, a ketone group, an ester group or a halogeno group, and $R^1$ and $R^2$ have the same meanings as defined above.

5. The process according to any one of claims 1 to 4, wherein the ruthenium complex is $Ru_3(CO)_{12}$.

6. The process according to claim 5, wherein $Ru_3(CO)_{12}$ is used in an amount of 0.1 to 10 mol-%.

7. The process according to any one of claims 1 to 6, wherein the reaction is conducted in a reaction medium comprising an acid or an ammonium salt thereof.

8. The process according to claim 7, wherein the acid or an ammonium salt thereof is used in an amount of 3 equivalents or more relative to $Ru_3(CO)_{12}$ (1 equivalent or more relative to the ruthenium atom).

9. The process according to claim 7 or 8, wherein the acid or an ammonium salt thereof is a salt consisting of an acid and the aromatic primary amine used in the reaction.

10. The process according to any one of claims 1 to 9, wherein the reaction is conducted under heating at 80 to 200° C.

11. The process according to claim 1, which comprises allowing an alkyne alcohol represented by formula (4);

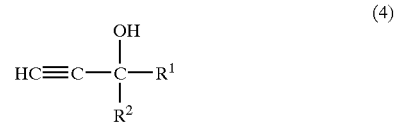

(4)

wherein $R^1$ and $R^2$ have the same meanings as defined above, to react with an aromatic primary amine in the presence of a ruthenium complex and in the coexistence of an acid or an ammonium salt thereof in an amount of 1 to 10 equivalents relative to the ruthenium atom, to form a compound represented by formula (5):

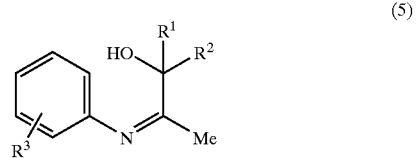

(5)

wherein $R^1$, $R^2$ and $R^3$ have the same meanings as defined above, then isolating the compound and adding an additional ruthenium complex and an acid or an ammonium salt thereof to react with the compound, or adding an acid or an ammonium salt thereof to react with the compound without isolation in the same system.

* * * * *